United States Patent
Caspi et al.

(10) Patent No.: US 10,898,713 B2
(45) Date of Patent: Jan. 26, 2021

(54) USES FOR EYE TRACKING IN A VISUAL PROSTHESIS

(71) Applicant: Second Sight Medical Products, Inc., San Fernando, CA (US)

(72) Inventors: Avraham I Caspi, Rehovot (IL); Jessy D Dorn, Los Angeles, CA (US); Arup Roy, Valencia, CA (US); Robert J Greenberg, Los Angeles, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 74 days.

(21) Appl. No.: 15/439,746

(22) Filed: Feb. 22, 2017

(65) Prior Publication Data

US 2017/0239477 A1 Aug. 24, 2017

Related U.S. Application Data

(60) Provisional application No. 62/298,390, filed on Feb. 22, 2016.

(51) Int. Cl.
*A61N 1/36* (2006.01)
*A61N 1/05* (2006.01)

(52) U.S. Cl.
CPC ....... *A61N 1/36046* (2013.01); *A61N 1/0543* (2013.01)

(58) Field of Classification Search
None
See application file for complete search history.

(56) References Cited

U.S. PATENT DOCUMENTS

| | | | |
|---|---|---|---|
| 4,628,933 A | 3/1986 | Michelson | |
| 4,573,481 A | 12/1986 | Bullara | |
| 4,837,049 A | 6/1989 | Byers et al. | |
| 5,109,844 A | 5/1992 | de Juan, Jr. et al. | |
| 5,215,088 A | 6/1993 | Normann et al. | |
| 5,935,155 A | 8/1999 | Humayun et al. | |
| 6,400,989 B1 | 6/2002 | Eckmiller | |
| 6,458,157 B1 | 10/2002 | Suaning | |
| 7,574,263 B2 | 8/2009 | Greenberg et al. | |
| 9,101,279 B2 * | 8/2015 | Ritchey | G16H 40/63 |
| 9,186,507 B2 | 11/2015 | Roy et al. | |

(Continued)

OTHER PUBLICATIONS

Daganelie, G., R.W. Massof, "Toward an Artificial Eye," IEEE Spectrum, May 1996. www.ieeexplore.ieee.org.

*Primary Examiner* — Ankit D Tejani
(74) *Attorney, Agent, or Firm* — Scott Dunbar

(57) ABSTRACT

The present invention is an improved system for use of eye tracking including spatial mapping percepts in a visual prosthesis by presenting an electrically induced precept through a visual prosthesis, requesting a subject look to the direction of the percept and tracking their eye movement. Eye movement is both faster and more accurate than asking a visual prosthesis user to point to the location of a percept. This method can be beneficial in a retinal prosthesis, but is particularly useful in a cortical visual prosthesis where visual cortex does not match the retinotopic map. Methods are presented for calibrating an eye tracker. Eye tracking hardware may also be used for blanking video information base on the subject's natural blink reflex.

6 Claims, 17 Drawing Sheets

(56) References Cited

U.S. PATENT DOCUMENTS

| | | | |
|---|---|---|---|
| 2010/0094382 A1* | 4/2010 | Pezaris | A61N 1/36046 607/54 |
| 2014/0107777 A1* | 4/2014 | Portney | A61F 2/1635 623/5.11 |
| 2014/0188222 A1* | 7/2014 | Gefen | A61N 1/36046 623/6.11 |
| 2014/0375782 A1* | 12/2014 | Chichilnisky | G06K 9/00671 348/62 |
| 2015/0342723 A1* | 12/2015 | Abramson | A61F 2/141 623/6.64 |

* cited by examiner

USES FOR EYE TRACKING IN A VISUAL PROSTHESIS

CROSS REFERENCE TO RELATED APPLICATIONS

This application incorporates by reference and claims priority to U.S. Provisional Application 62/298,390, for Spatial Mapping in a Visual Prosthesis by Tracking Eye Movement, filed Feb. 22, 2016.

TECHNICAL FIELD

The present disclosure relates to visual prostheses configured to provide neutral stimulation for the creation of artificial vision, and more specifically, new uses for eye tracking including an improved method of spatial mapping by tracking eye movement in a visual prosthesis and other applications of an eye tracker in a visual prosthesis.

BACKGROUND

A visual prosthesis is an electronic neural stimulator that stimulates visual percepts with an array of electrodes, typically on the retina, LNG or visual cortex. Current technology for implantable neural stimulators and electrode arrays is quite limited, while high resolution video cameras are quite inexpensive. Cameras are typically mounted on the head, such as on a pair of glasses. This causes the user to scan with their head to observe a scene. It was suggested in 1996 (see Toward an Artificial Eye, IEEE Spectrum May 1996) that an eye tracker can be used to move the prosthesis field of view around a scene output by the camera to obtain more natural scanning by the visual prosthesis user.

U.S. Pat. No. 7,574,263 teaches methods correcting spatial distortions in a visual prosthesis. While U.S. Pat. No. 7,574,263 teaches how to correct distortions, the method is manual and time consuming.

U.S. Pat. No. 9,186,507 teaches that constant stimulation of neural tissue results in a gradual fading of percepts. It is advantageous to provide occasional breaks in neural stimulation to reset the neural pathway.

SUMMARY

The present invention is an improved system for use of eye tracking including spatial mapping percepts in a visual prosthesis by presenting an electrically induced precept through a visual prosthesis, requesting a visual prosthesis user (subject) look to the direction of the percept and tracking their eye movement. Eye movement is both faster and more accurate than asking a subject to point to the location of a percept. This method can be beneficial in a retinal prosthesis, but is particularly useful in a cortical visual prosthesis where visual cortex does not match the retinotopic map. Methods are presented for calibrating an aligning an eye tracker. Eye tracking hardware may also be used for blanking video information base on the subject's natural blink reflex.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIGS. 12-1, 12-2, 12-3 and 12-4 show an exemplary embodiment of a video processing unit. FIG. 12-1 should be viewed at the left of FIG. 12-2. FIG. 12-3 should be viewed at the left of FIG. 12-4. FIGS. 12-1 and 12-2 should be viewed on top of FIGS. 12-3 and 12-4.

DETAILED DESCRIPTION

The present invention includes an improved spatial fitting and mapping system for a visual prosthesis. The system of the present invention maps projected locations of percepts, where a person perceives a percept from a visual prosthesis to the intended location of the percepts. The projected location may vary over time. This test results can be used to correct a visual prosthesis or spatially map the visual prosthesis.

Figure 1:
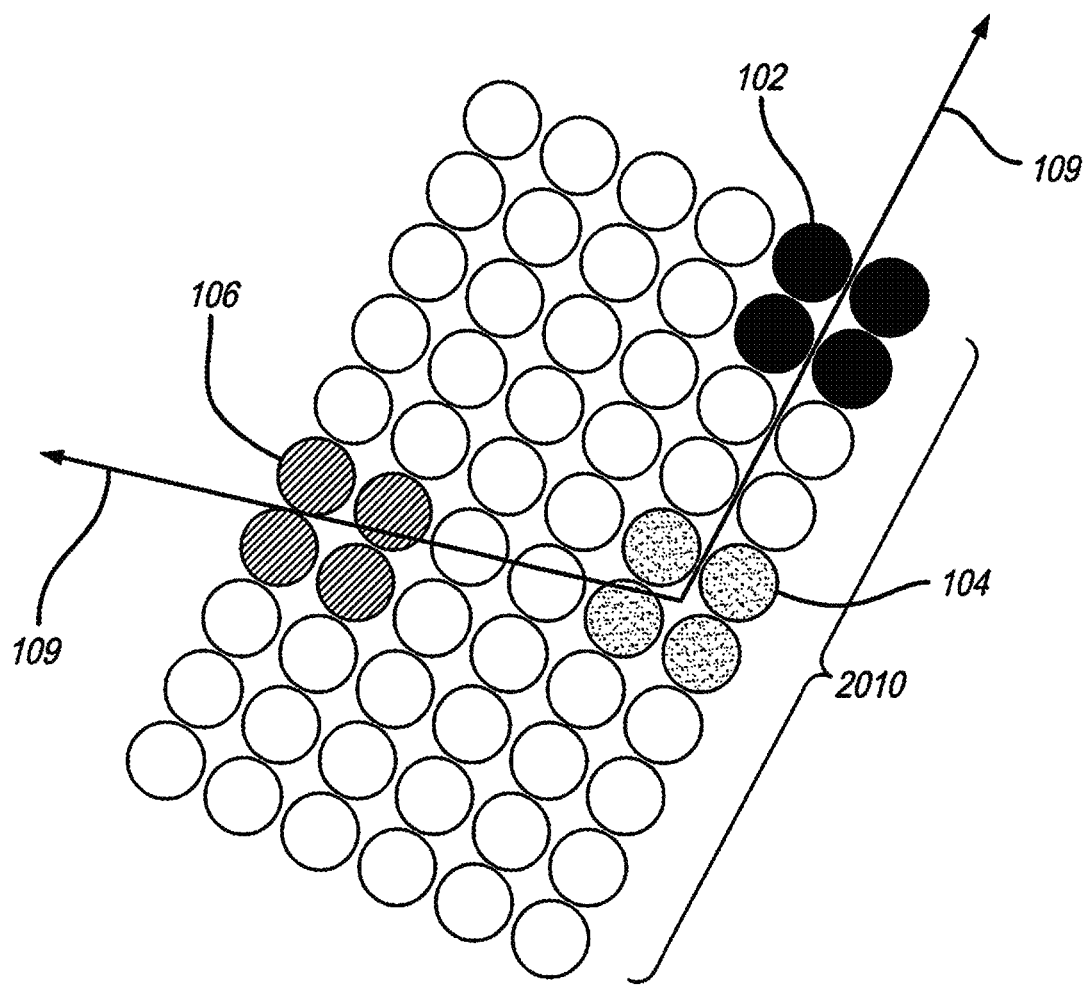
FIG. 1 shows a schematic view of an electrode array indicating a first stimulation test.

FIG. 1 shows a schematic view of an electrode array indicating a first stimulation test. Note that the image of the electrodes is tilted to match the observed tilt of the electrode array on a retina. Each test includes three stimulation patterns 102, 104 and 106.

Figure 2:
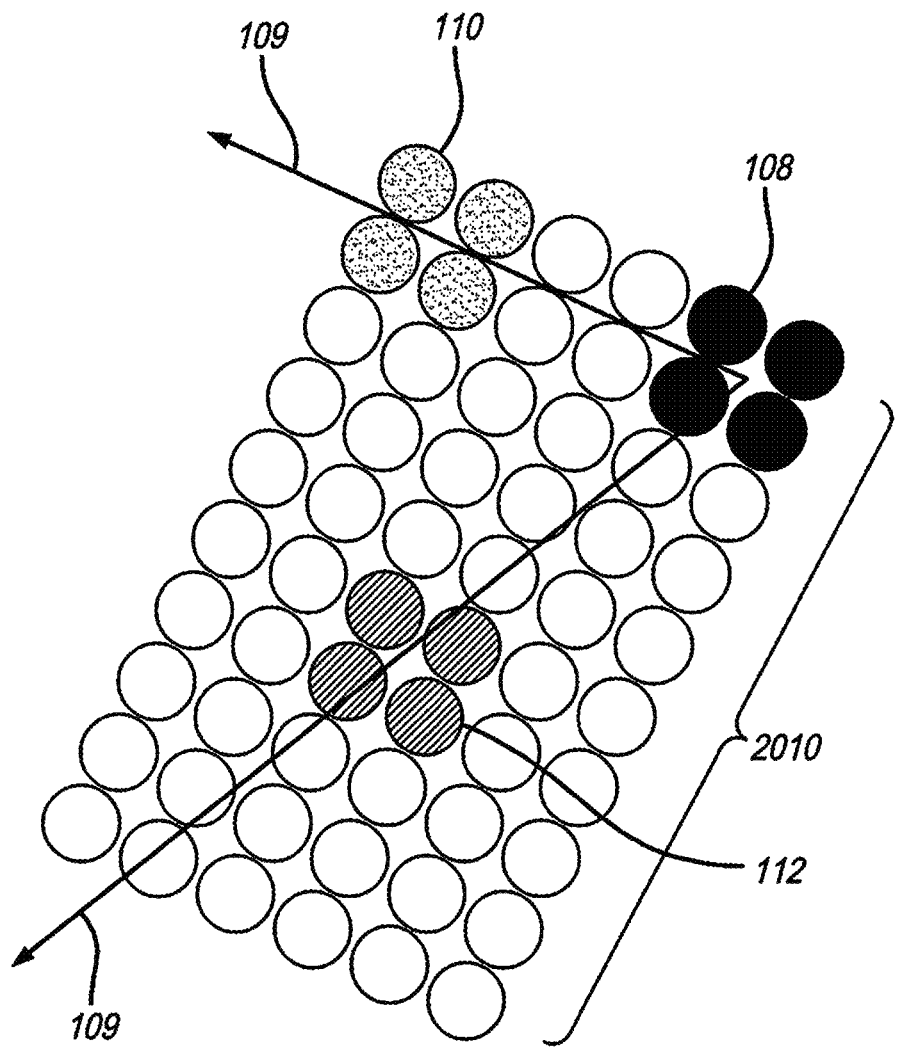
FIG. 2 shows a schematic view of an electrode array indicating a second stimulation test.

FIG. 2 shows a schematic view of an electrode array indicating a second stimulation pattern. Again the array has the same tilt. The second test includes patterns 108, 110, and 112.

Figure 3:
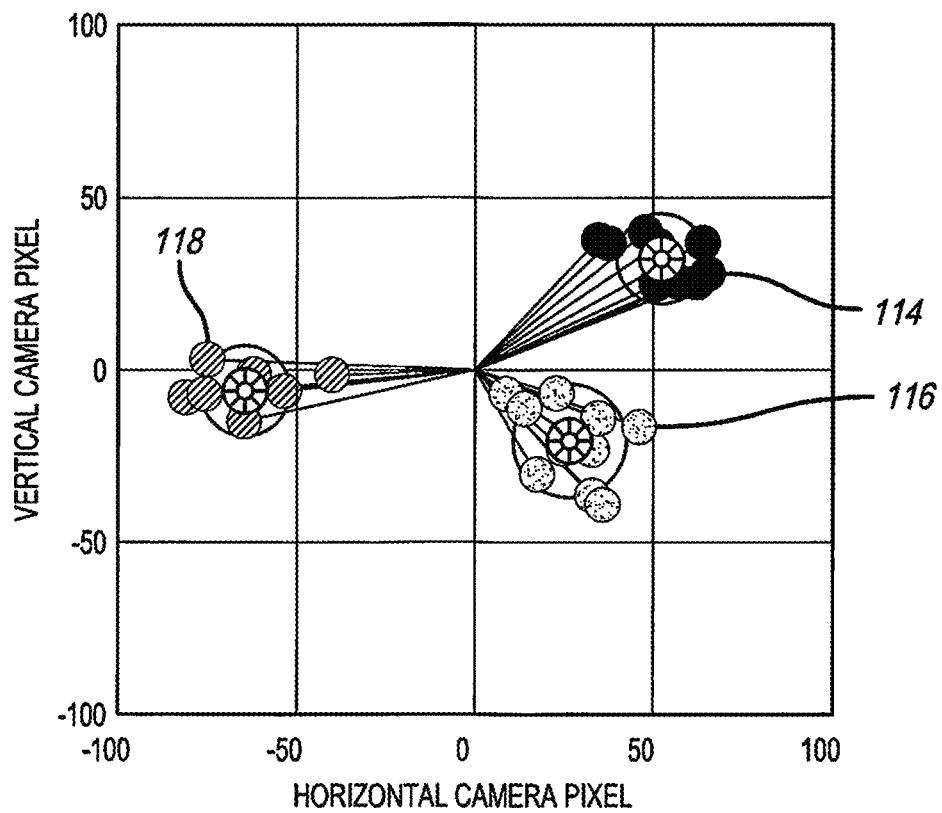
FIG. 3 shows the pupil's relative location between the start and end of the first stimulation test.

FIG. 3 shows the pupil's relative location between the start and end of the trial with the first stimulation pattern. In each case the subject is asked to begin by look straight forward, and the look toward the location of a percept. Stimulation pattern 102 induces eye movement 114; stimulation pattern 104 includes eye movement 116, and stimulation pattern 106 induces eye movement 118.

Figure 4:
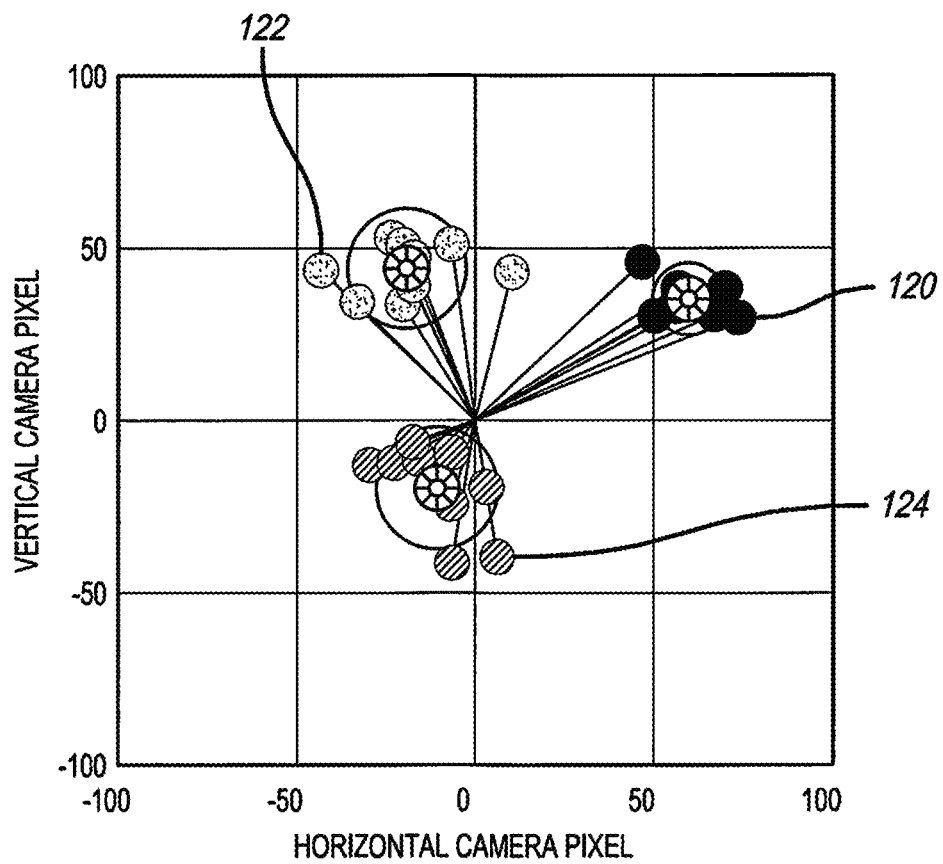
FIG. 4 shows the pupil's relative location between the start and end of the second stimulation test.

FIG. 4 shows the pupil's relative location between the start and end of the trial with the second stimulation pattern. In each case the subject is asked to begin by look straight forward, and the look toward the location of a percept. Stimulation pattern 108 induces eye movement 120; stimulation pattern 110 includes eye movement 122, and stimulation pattern 112 induces eye movement 124.

Figure 5:
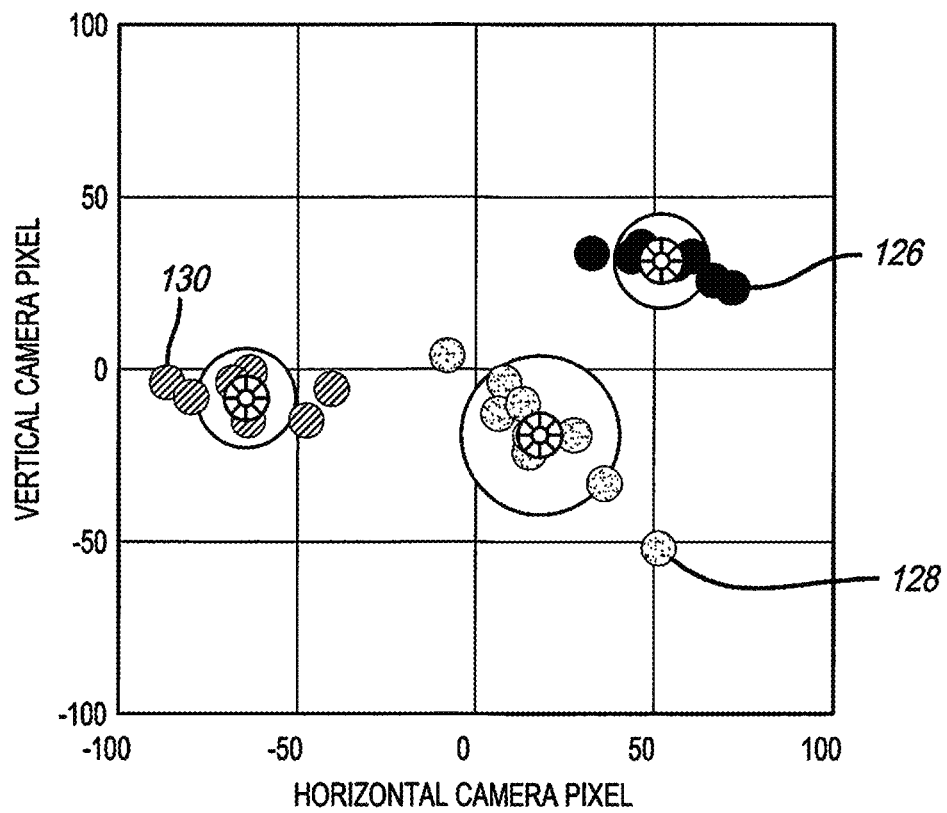
FIG. 5 shows the pupil's absolute location at the end of the first stimulation test.

FIG. 5 shows the pupil's absolute location at the end of the trial with the first stimulation pattern. Stimulation pattern 102 induces a percept at location 126; stimulation pattern 104 includes a percept at location 128, and stimulation pattern 106 induces a percept at location 130.

Figure 6:
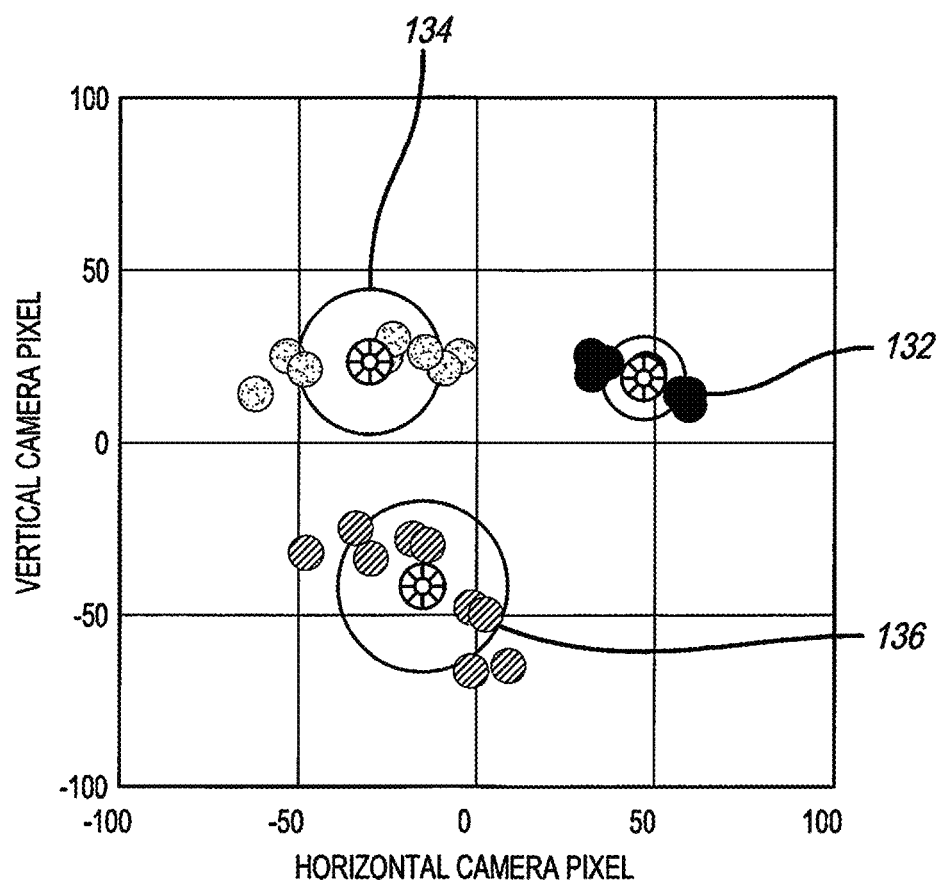
FIG. 6 shows the pupil's absolute location at the end of the second stimulation test.

FIG. 6 shows the pupil's absolute location at the end of the trial with the second stimulation pattern. Stimulation pattern 108 induces a percept at location 132; stimulation pattern 110 includes a percept at location 134, and stimulation pattern 112 induces a percept at location 136.

The data shown in FIGS. 1-6 is the result of experiments conducted by the applicants. The experimental setup consisted of two computers that were powered by the internal batteries. The first computer generated the stimulation patterns shown in FIGS. 1 and 2, and the second recorded video images of the pupil shown in FIGS. 3 through 6. Pupil recording and stimulation had synchronized timestamps. Stimulation patterns for each trial were created to stimulate four electrodes. A binary large object (BLOB) image was created on the computer using MATLAB and delivered to the Argus II system by connecting to the camera port using a VGA to NTSC adapter (Startech, VGA2VID). The image was such that there was white level over the four stimulated electrodes while the rest of the image was black. Pupil images were acquired at 30 frames per second using a USB camera (Microsoft, HD-6000) with an IR pass filter to block the room lighting in the visible spectrum. The pupil was illuminated by an IR LED (Osram, SFH 4050-Z). The pupil camera was mounted on a modified Pupil Lab frame (www.pupil-labs.com). The transmission coil of the Argus II (see FIG. 1) was taped to the Pupil Lab frame. We didn't use the Argus II eye-wear since the stimulation patterns were created in the computer and there was no need for the camera. The stimulation pattern images were delivered to the recording computer using a VGA to USB adapter (Epiphan, DVI2USB3.0). The video streams from the pupil camera and the stimulation pattern were streamed and saved on the recording computer that had a Linux (Ubuntu 14.02) operating system. In addition to the video files, the application saved a META file with a timestamp for each frame.

Stimulation waveforms on each electrode were set according to the programming that is used by the patient in daily activities with the Argus II.

In each session, three patterns were interleaved and each pattern consisted of four neighboring electrodes. Stimulation duration was set to 0.6 s and the patient was instructed to move her eye to where she saw the light. The patient was remind to look straight at beginning of each trial.

For each trial, we located the pupil frames at the time of the stimulation. The frames were presented on the computer (for example, see FIGS. 3-6). We manually marked the pupil location at the beginning of the stimulation and in a resting position after the eye moved to the percept's location. It is worthwhile to note that data is presented in pixel coordinates of the pupil camera and not in degrees of gaze position. In order to convert the pupil location to pixel coordinates, the eye tracker had to be calibrated which is not trivial for blind patients (see FIG. 7).

FIGS. 1-6 shows examples of two sessions in which three different patterns where measured in each session. FIGS. 1 and 2 show the array's layout with the electrodes that were stimulated in each session. The layout was rotated to account for the placement as measured by fundus imaging. The electrodes are pattern grouped, indicating the four electrodes that were stimulated in each trial. FIGS. 3 and 4 show the relative spatial map, calculated as the difference in pupil position from the beginning of the trial to the end of the trial. In this case, the data were adjusted so that location of the pupil at the beginning of the trial was defined as the origin (0, 0). FIGS. 5 and 6 show the absolute spatial map, as calculated by the absolute pupil location at the end of the trial. In this case, we ignored the pupil location at the beginning of the trial. For convenience sake, the pupil locations were adjusted so that the average across all patterns in all trials was at the origin.

It can be seen that the spreads of the marked locations in the relative analysis (FIGS. 3 and 4) method are narrower compared to the absolute case (FIGS. 5 and 6). Comparing the standard error of the pupil location between the relative and absolute methods using a paired t-test showed a significance of $p=0.03$.

In order to quantify the measured spatial map, we compared the relative orientation between the vectors 109 in FIGS. 1 and 2. For the first session the angle between the vectors, calculated from the layout of the array, is 101 deg. compared to 107 deg. that was calculated based on the measured spatial map. For the second session the angle between the vectors calculated from the layout of the array is 59 deg. compared to 50 deg. that was calculated from the measured spatial map. The relatively small discrepancy of 6 and 9 deg. in the measured orientation can be attributed to the fact that we estimated the orientation from pupil location and not from gaze orientation. The scaling on the horizontal and vertical dimensions from pupil location to gaze orientation probably is not the same. It is worthwhile to mention that the differences between theoretical and measured vector orientations are better than the average response error of a motion detection task of good performing implanted patients. Our experiment shows the feasibility in using eye movements as markers to measure the spatial mapping of a visual prosthesis. We observed that the relative pupil location is more confined relative to the absolute pupil location. This suggests that patients perceive the location of the phosphene relative to the instantaneous gaze position at the time of the stimulation. The relative location of the patterns we mapped matches the location on the array. Hence, the oculomotor system of a blind patient still functions and the patient can direct the gaze to the location of the phosphene.

An eye tracker can be calibrated for blind patients. For example, we will analyze the glint of an array of LEDs in addition to pupil location. However, data presented here shows that we can spatially map the percept of a visual implant based on pupil location without gaze calibration.

Figure 7:
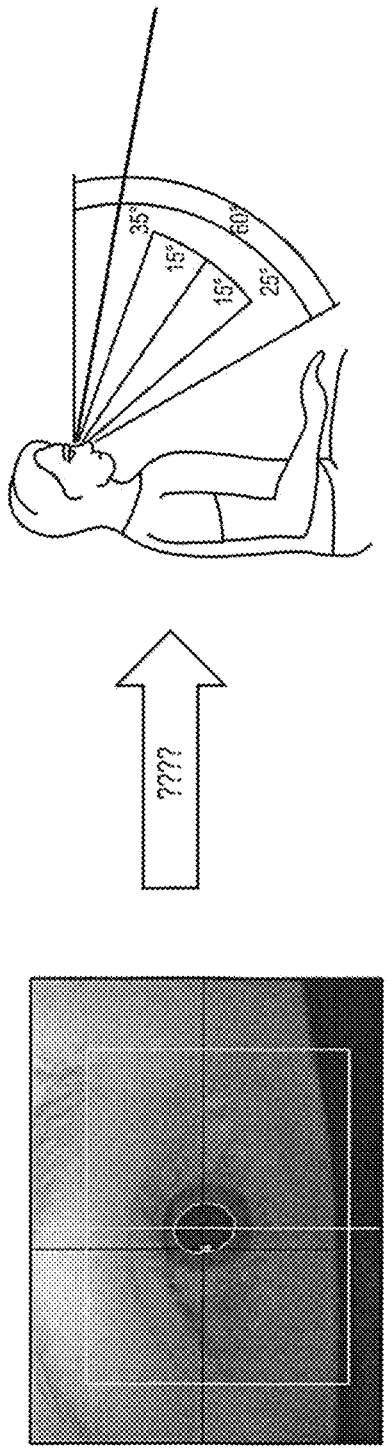
FIG. 7 shows the relationship of eye position to direction of gaze.

Referring to FIG. 7, in order to calibrate an eye tracker with a blind user of a visual prosthesis, i.e. finding the parameters that will convert pupil coordinates to world coordinates, we perform the following:
1. Have a system that will acquire pupil location and scene, front-facing camera with timestamps synchronized with stimulation of the visual prosthesis.
2. The world camera will be used to measure the location of the percept by locating the position of a hand-held marker in the space.
3. The system will stimulate a group of electrodes and ask the patient to place a hand-held marker that will mark the location of the perceived stimulation.
4. Repeat step #1 for several eye positions.
5. Based on the transformation model between pupil and gaze coordinates, find the parameters that will minimize the spread of pattern location for each group of electrodes.

The parameters that were found will be used to convert pupil to gaze in order to steer the line-of-sight of the prosthesis in real-time.

The location of the percept due to an electrical stimulation is a function of two factors:
The location of the stimulation on the retina and
The orientation of the eyeball (i.e. gaze).

$$X_{world}(p,i) = X_{implant}^0 + X_{pattern}^0(p) + X_{gaze}^0(i)$$

$$Y_{world}(p,i) = Y_{implant}^0 + Y_{pattern}^0(p) + Y_{gaze}^0(i)$$

Where:
$X_{pattern}^0(p); Y_{pattern}^0(p)$ the location of a pattern p relative to the center of the implanted array
$X_{implant}^0; Y_{implant}^0$ implant the location of a pattern p relative to the center of the implanted array
$X_{gaze}(i); Y_{gaze}(i)$ the location of a pattern p relative to the center of the implanted array
$X_{precept}(p,i); Y_{precept}(p,i)$ the location of a pattern p relative to the center of the implanted array Simple Model:

$$X_{gaze}(i) = a_1 \cdot X_{pupil}(i) + a_0$$

$$Y_{gaze}(i) = b_1 \cdot Y_{pupil}(i) + b_0$$

Need to find four independent variables $a_0, a_1, b_0, b_1$
Advance Model:

$$X_{gaze}(i) = a_1 \cdot X_{pupil}(i) + a_2 \cdot Y_{pupil}(i) + a_0$$

$$Y_{gaze}(i) = b_1 \cdot Y_{pupil}(i) + b_2 \cdot X_{pupil}(i) + b_0$$

Need to find six independent variables $a_0, a_1, a_2, b_0, b_1, b_2$
We will get for the simple model:

$$X_{world}(p,i) = X_{implant}^0 + X_{pattern}^0(p) + a_1 \cdot X_{pupil}(i) + a_0$$

$$Y_{world}(p,i) = Y_{implant}^0 + Y_{pattern}^0(p) + b_1 \cdot Y_{pupil}(i) + b_0$$

Or for the advanced model:

$$X_{world}(p,i) = Y_{implant}^0 + X_{pattern}^0(p) + a_1 \cdot X_{pupil}(i) + a_2 \cdot Y_{pupil} + a_0$$

$$Y_{world}(p,i) = Y_{implant}^0 + Y_{pattern}^0(p) + b_1 \cdot Y_{pupil}(i) + b_2 \cdot X_{pupil} + b_0$$

Figure 8A:
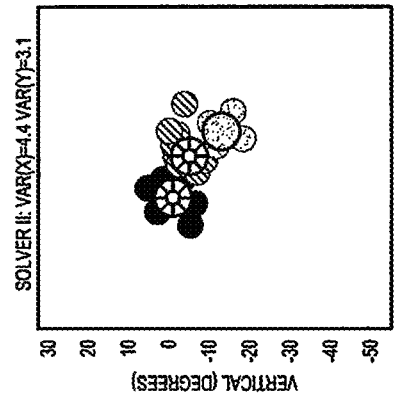
FIG. 8A shows recorded data without eye movement correction, shading matches the stimulation groups in the FIG. 8B
Figure 8C:
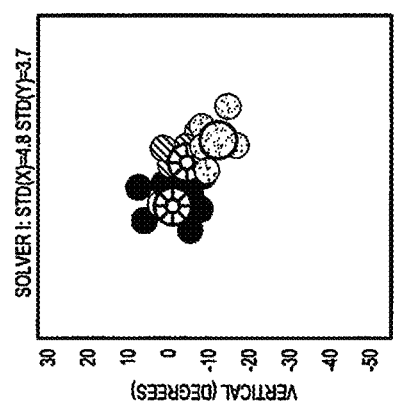
FIG. 8C shows correction according to pupil location based on the simple model while coefficients were calculated based on linear regression.
Figure 8E:
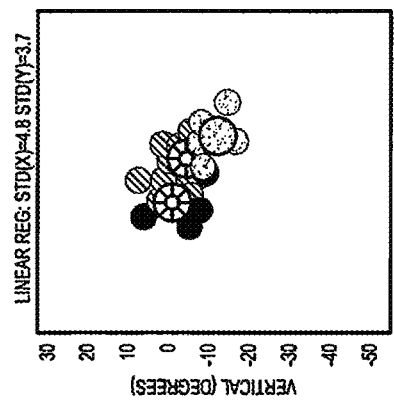
FIG. 8E shows correction according to pupil location based on the simple model while coefficients were calculated based on a solver algorithm.
Figure 8G:
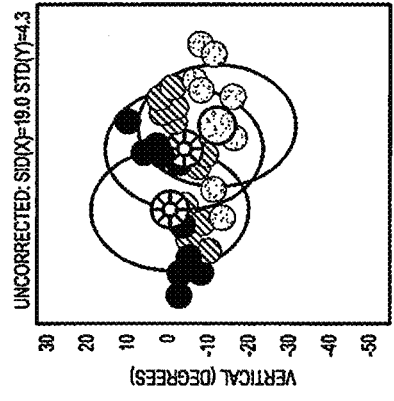
FIG. 8G shows correction according to pupil location based on the simple model while coefficients were calculated based on a solver algorithm.
Figure 8B:
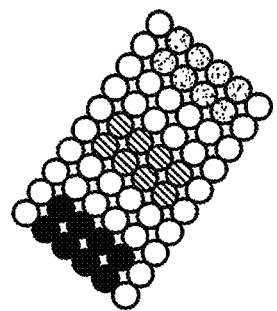
FIG. 8B shows a schematic view of an electrode array include electrodes being stimulated.
Figure 8D:
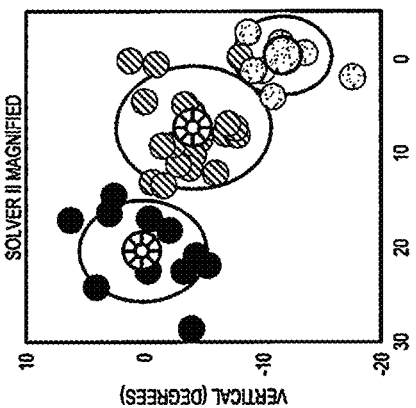
FIG. 8D is a magnified version of FIG. 8C.
Figure 8F:
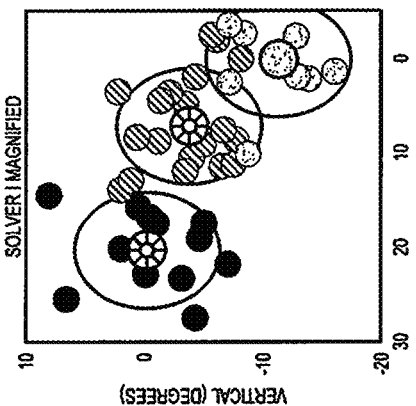
FIG. 8F is a magnified version of FIG. 8E.
Figure 8H:
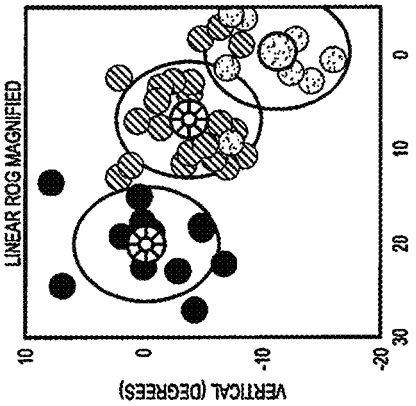
FIG. 8H is a magnified version of FIG. 8G.

$X_{pattern}^0(p); Y_{pattern}^0(p)$
Is the theoretical of percept's location that pattern p will generate in coordinates relative to line-of-sight of the retina
$X_{world}(p,i); Y_{world}(p,i)$
Mark the theoretical location of the percept at trial i when pattern p is on Moving to real life
$X_{world}(p,i); Y_{world}(p,i)$
Is the actual percept's location that pattern p generated at trial i in coordinates array relative to line-of-sight of the retina
$X_{world}^M(p,i); Y_{world}^M(p,i)$
Mark the measured location of the percept at trial i when pattern p is on Preliminary results of patient testing is shown in FIG. 8:

FIG. 8A shows recorded data without eye movement correction, patterns match the stimulation groups in FIG. 8B, note that the marked location for each group is not distinct.
FIG. 8B shows electrodes stimulated on the array.
FIG. 8C shows correction according to pupil location based on the simple model while coefficients where calculated based on linear regression. FIG. 8D is a magnified version of FIG. 8C.
FIG. 8E shows correction according to pupil location based on the simple model while coefficients where calculated based on a solver algorithm. FIG. 8F is a magnified version of FIG. 8E.
FIG. 8G shows correction according to pupil location based on the simple model while coefficients where calculated based on a solver algorithm. FIG. 8H is a magnified version of FIG. 8G.
The layout of the array with the stimulated groups was rotated to account for the placement of the array on the retina.

For spatial fitting purposes, only the average value of the many trails is important. As can be seen in FIGS. 8A through 8H, tests produce a range of values. The spread of these values can be used to guide down sampling. As noted above, the camera produced a much higher resolution image than the available electrode array. To get from the higher resolution camera to the lower resolution electrode array, down sampling is required. The range of the test samples is indicative of the area the subject perceives as the same place and indicative of the number of camera pixels that can be assigned to a single electrode.

When eye tracking for spatial fitting or for normal use to alter video data according to the gaze of the eye, it is important record only when the eye is stationary. In addition to intentional eye movement to look at something the eye constantly moves in involuntary micro-saccades. An eye tracking camera does not measure eye movement, but samples eye location at regular intervals. Regardless of the sample rate, samples at the same location for more than 50 milliseconds indicate the end of the eye movement or saccade.

As described in U.S. Pat. No. 9,186,507, stimulation of neural percepts fade with continuous stimulation. The 507 patent teaches multiple ways of interrupting stimulation to reset neural pathways. An eye tracking camera can also function as a blink detector. Interrupting stimulation each time the eye lid closes provides a natural reset of the neural pathways. It should be clear to one of skill in the art that other blink detectors are possible such as a light detector that measure the reduction of reflected light of the eye lid versus the eye or an electrical sensor that senses activation of the eye lid muscle. In additional to the reset of a natural blink, this is give visual prosthesis user an intuitive way to stop stimulation such as in response to a bright light or fatigue. A range of physiological changes may be detected and used to trigger an interruption of stimulation. A saccade can also be used as a signal to interrupt stimulation. Stimulation of an image mid-saccade provides little benefit and may be confusing to the user. It should also be noted that eye tracking sensors other than a camera can also be used.

Figure 9:
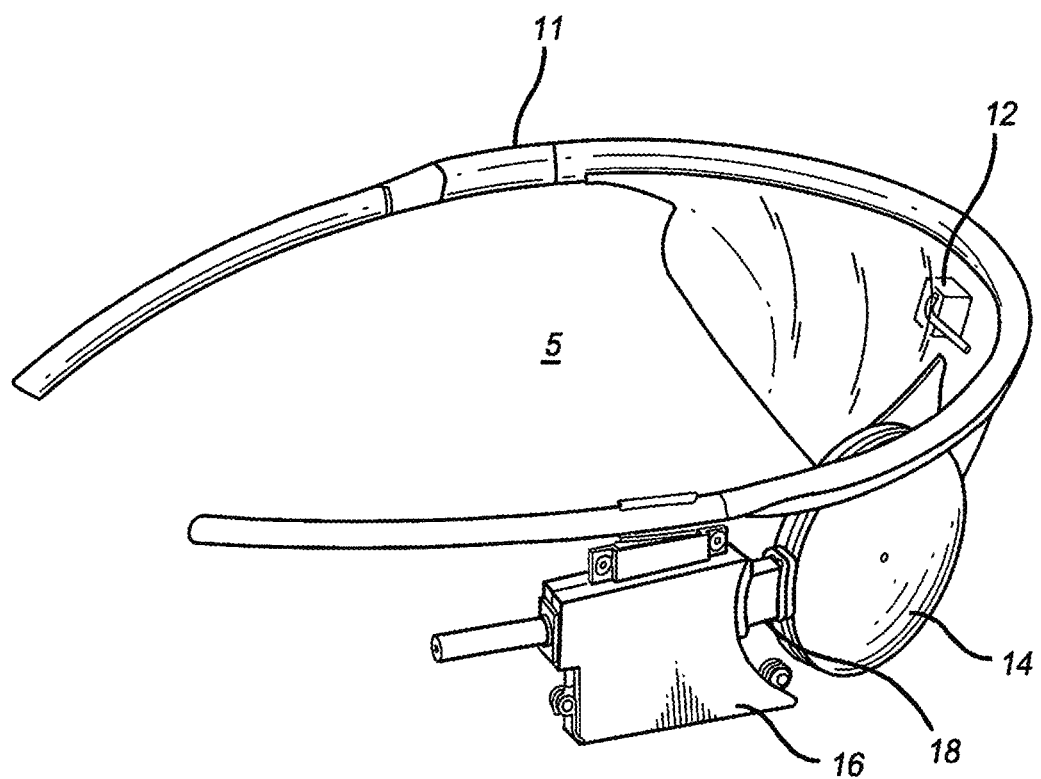
FIG. 9 show a video capture/transmission apparatus or visor adapted to be used in combination with the retinal stimulation of FIGS. 16 and 17.

Referring to FIG. 9, the glasses 5 may comprise, for example, a frame 11 holding a camera 12, an external coil 14 and a mounting system 16 for the external coil 14. The mounting system 16 may also enclose the RF circuitry. In this configuration, the video camera 12 captures live video. The video signal is sent to an external Video Processing Unit (VPU) 20 (shown in FIGS. 10, and 11 and discussed below), which processes the video signal and subsequently transforms the processed video signal into electrical stimulation patterns or data. The electrical stimulation data are then sent to the external coil 14 that sends both data and power via radio-frequency (RF) telemetry to the coil 2016 of the retinal stimulation system 1, shown in FIG. 13. The coil 2016 receives the RF commands which control the application specific integrated circuit (ASIC) which in turn delivers stimulation to the retina of the subject via a thin film electrode array (TFEA). In one aspect of an embodiment, light amplitude is recorded by the camera 12. The VPU 20 may use a logarithmic encoding scheme to convert the incoming light amplitudes into the electrical stimulation patterns or data. These electrical stimulation patterns or data may then be passed on to the Retinal Stimulation System 1, which results in the retinal cells being stimulated via the electrodes in the electrode array 2010 (shown in FIG. 13). In one exemplary embodiment, the electrical stimulation patterns or data being transmitted by the external coil 14 is binary data. The external coil 14 may contain a receiver and transmitter antennae and a radio-frequency (RF) electronics card for communicating with the internal coil 2016.

Figure 10:
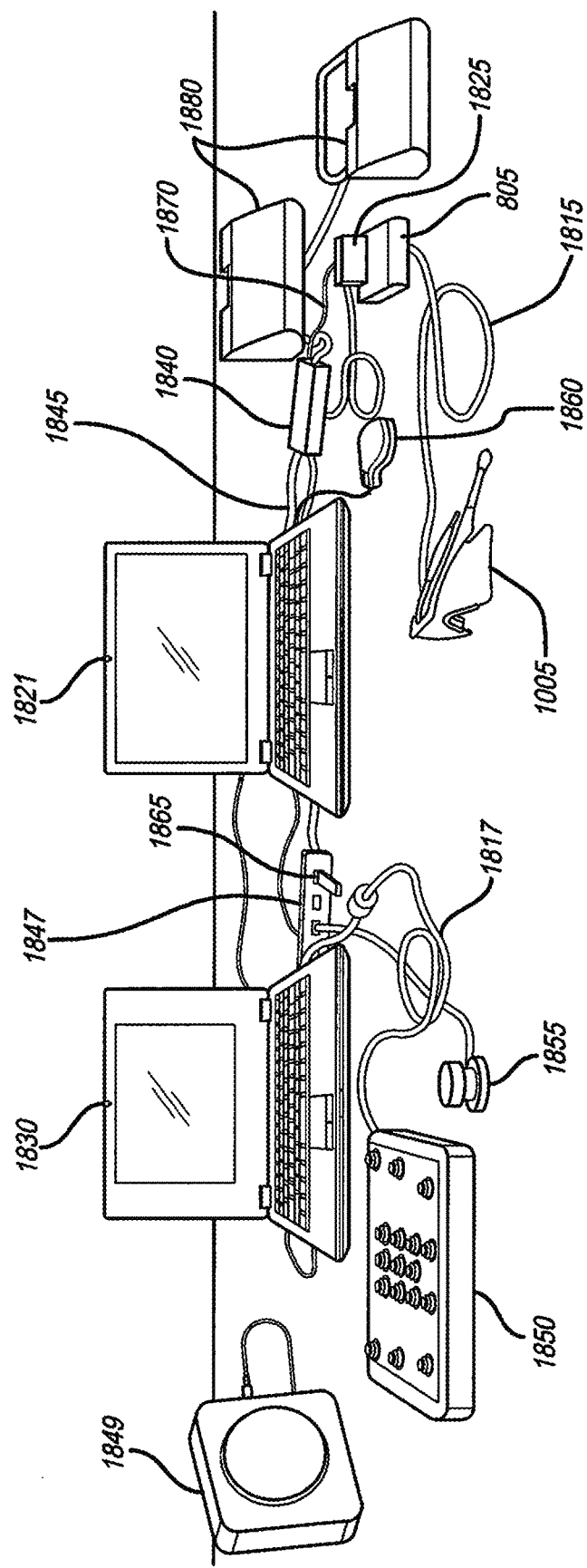
FIG. 10 shows components of a fitting system according to the present disclosure, the system also comprising the visor shown in FIGS. 6 and 7.
Figure 13:
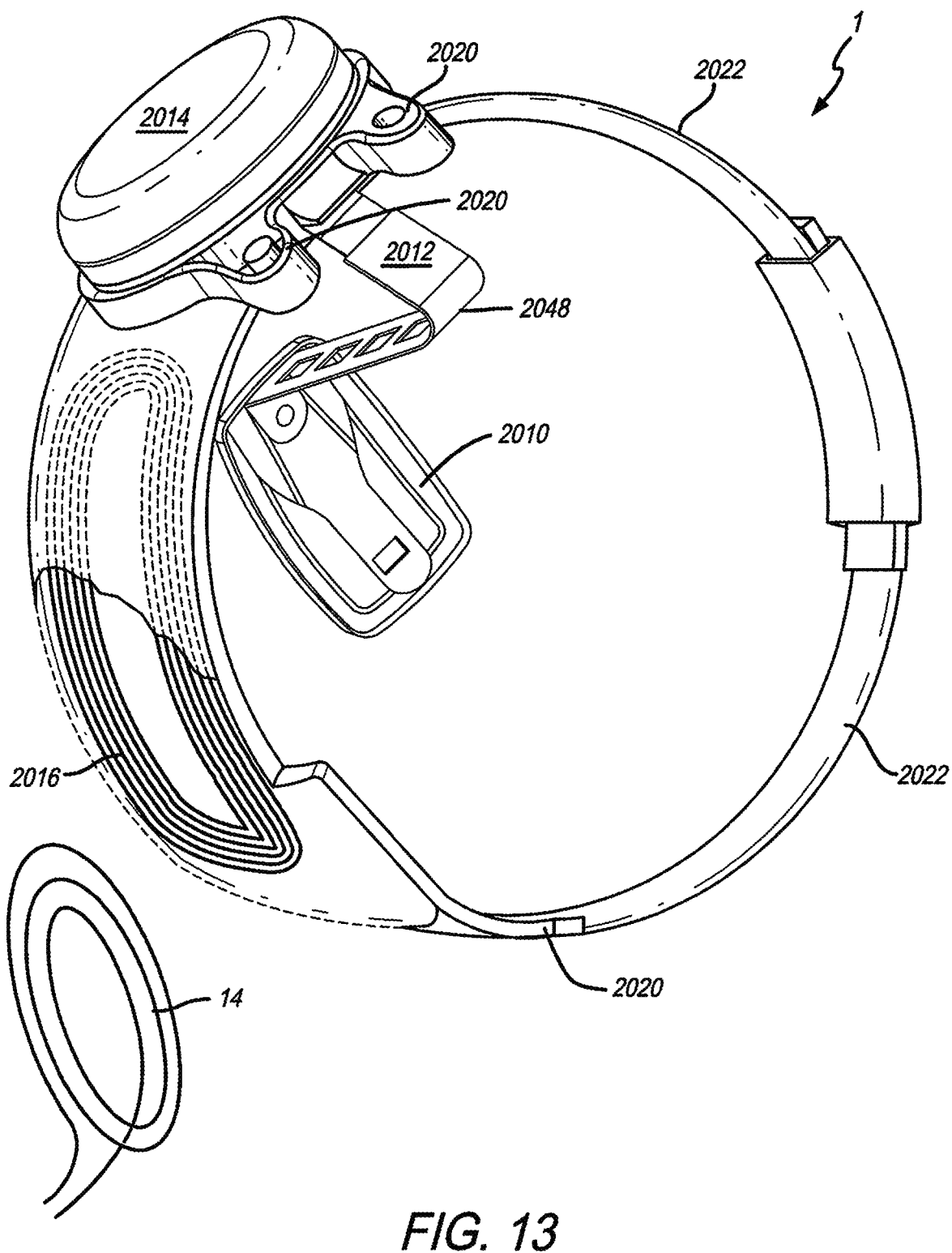
FIG. 13 is a perspective view of the implanted portion of the preferred visual prosthesis.

Referring to FIG. 10, a Fitting System (FS) may be used to configure and optimize the visual prosthesis apparatus shown in FIG. 13. The Fitting System is fully described in the related application U.S. application Ser. No. 11/796,425, filed on Apr. 27, 2007, which is incorporated herein by reference in its entirety.

The Fitting System may comprise custom software with a graphical user interface running on a dedicated laptop computer 10. Within the Fitting System are modules for performing diagnostic checks of the implant, loading and executing video configuration files, viewing electrode voltage waveforms, and aiding in conducting psychophysical experiments. A video module can be used to download a video configuration file to the Video Processing Unit (VPU) 20 discussed above and store it in non-volatile memory to control various aspects of video configuration, e.g. the spatial relationship between the video input and the electrodes. The software can also load a previously used video configuration file from the VPU 20 for adjustment.

The Fitting System can be connected to the Psychophysical Test System (PTS), located for example on a dedicated laptop 30, in order to run psychophysical experiments. In psychophysics mode, the Fitting System enables individual electrode control, permitting clinicians to construct test stimuli with control over current amplitude, pulse-width, and frequency of the stimulation. In addition, the psychophysics module allows the clinician to record subject responses. The PTS may include a collection of standard psychophysics experiments developed using for example MATLAB® (MathWorks)™ software and other tools to allow the clinicians to develop customized psychophysics experiment scripts.

Using the psychophysics module, important perceptual parameters such as perceptual threshold, maximum comfort level, and spatial location of percepts may be reliably measured. Based on these perceptual parameters, the fitting software enables custom configuration of the transformation between video image and spatio-temporal electrode stimulation parameters in an effort to optimize the effectiveness of the visual prosthesis for each subject.

The Fitting System laptop 10 of FIG. 10 may be connected to the VPU 20 using an optically isolated serial connection adapter 40. Because it is optically isolated, the serial connection adapter 40 assures that no electric leakage current can flow from the Fitting System laptop 10 in the event of a fault condition.

As shown in FIG. 10, the following components may be used with the Fitting System according to the present disclosure. The Video Processing Unit (VPU) 20 for the subject being tested, a Charged Battery 25 for VPU 20, the Glasses 5, a Fitting System (FS) Laptop 10, a Psychophysical Test System (PTS) Laptop 30, a PTS CD (not shown), a Communication Adapter (CA) 40, a USB Drive (Security) (not shown), a USB Drive (Transfer) 47, a USB Drive (Video Settings) (not shown), a Patient Input Device (RF Tablet) 50, a further Patient Input Device (Jog Dial) 55, Glasses Cable 15, CA-VPU Cable 70, FS-CA Cable 45, FS-PTS Cable 46, Four (4) Port USB Hub 47, Mouse 60, Test Array system 80, Archival USB Drive 49, an Isolation Transformer (not shown), adapter cables (not shown), and an External Monitor (not shown).

With continued reference to FIG. 9, the external components of the Fitting System may be configured as follows. The battery 25 is connected with the VPU 20. The PTS Laptop 30 is connected to FS Laptop 10 using the FS-PTS Cable 46. The PTS Laptop 30 and FS Laptop 10 are plugged into the Isolation Transformer (not shown) using the Adapter Cables (not shown). The Isolation Transformer is plugged into the wall outlet. The four (4) Port USB Hub 47 is connected to the FS laptop 10 at the USB port. The mouse 60 and the two Patient Input Devices 50 and 55 are connected to four (4) Port USB Hubs 47. The FS laptop 10 is connected to the Communication Adapter (CA) 40 using the FS-CA Cable 45. The CA 40 is connected to the VPU 20 using the CA-VPU Cable 70. The Glasses 5 are connected to the VPU 20 using the Glasses Cable 15.

Figure 11:
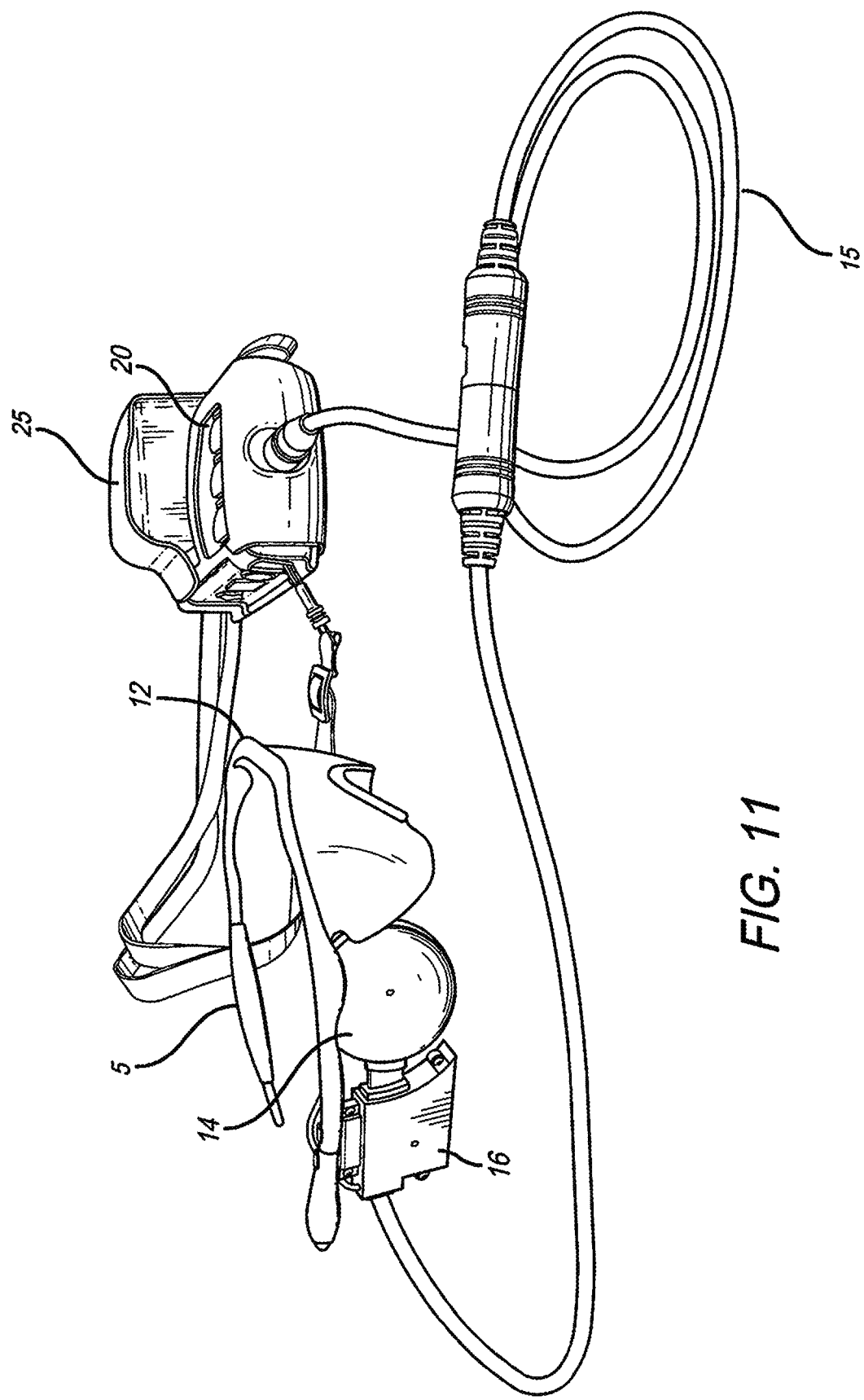
FIG. 11 shows the external portion of the visual prosthesis apparatus in a stand-alone mode, i.e. comprising the visor connected to a video processing unit.

In one exemplary embodiment, the Fitting System shown in FIG. 10 may be used to configure system stimulation parameters and video processing strategies for each subject outfitted with the visual prosthesis apparatus of FIG. 11. The fitting application, operating system, laptops 10 and 30, isolation unit and VPU 20 may be tested and configuration controlled as a system. The software provides modules for electrode control, allowing an interactive construction of test stimuli with control over amplitude, pulse width, and frequency of the stimulation waveform of each electrode in the Retinal stimulation system 1. These parameters are checked to ensure that maximum charge per phase limits, charge balance, and power limitations are met before the test stimuli are presented to the subject. Additionally, these parameters may be checked a second time by the VPU 20's firmware. The Fitting System shown in FIG. 10 may also provide a psychophysics module for administering a series of previously determined test stimuli to record subject's responses. These responses may be indicated by a keypad 50 and or verbally. The psychophysics module may also be used to reliably measure perceptual parameters such as perceptual threshold, maximum comfort level, and spatial location of percepts. These perceptual parameters may be used to custom configure the transformation between the video image and spatio-temporal electrode stimulation parameters thereby optimizing the effectiveness of the visual prosthesis for each subject. The Fitting System is fully described in the related application U.S. application Ser. No. 11/796,425, filed on Apr. 27, 2007, which is incorporated herein by reference in its entirety.

The visual prosthesis apparatus may operate in two modes: i) stand-alone mode and ii) communication mode Stand-Alone Mode Referring to FIG. 11, in the stand-alone mode, the video camera 12, on the glasses 5, captures a video image that is sent to the VPU 20. The VPU 20 processes the image from the camera 12 and transforms it into electrical stimulation patterns that are transmitted to the external coil 14. The external coil 14 sends the electrical stimulation patterns and power via radio-frequency (RF) telemetry to the implanted retinal stimulation system. The internal coil 2016 of the retinal stimulation system 1 receives the RF commands from the external coil 14 and transmits them to the electronics package 2014 that in turn delivers stimulation to the retina via the electrode array 2010. Additionally, the retinal stimulation system 1 may communicate safety and operational status back to the VPU 20 by transmitting RF telemetry from the internal coil 2016 to the external coil 14. The visual prosthesis apparatus of FIG. 11 may be configured to electrically activate the retinal stimulation system 1 only when it is powered by the VPU 20 through the external coil 14. The stand-alone mode may be used for clinical testing and/or at-home use by the subject.

Communication Mode

The communication mode may be used for diagnostic testing, psychophysical testing, patient fitting and downloading of stimulation settings to the VPU 20 before transmitting data from the VPU 20 to the retinal stimulation system 1 as is done for example in the stand-alone mode described above. Referring to FIG. 10, in the communication mode, the VPU 20 is connected to the Fitting System laptop 10 using cables 70, 45 and the optically isolated serial connection adapter 40. In this mode, laptop 10 generated stimuli may be presented to the subject and programming parameters may be adjusted and downloaded to the VPU 20. The Psychophysical Test System (PTS) laptop 30 connected to the Fitting System laptop 10 may also be utilized to perform more sophisticated testing and analysis as fully described in the related application U.S. application Ser. No. 11/796,425, filed on Apr. 27, 2007, which is incorporated herein by reference in its entirety.

In one embodiment, the functionality of the retinal stimulation system can also be tested pre-operatively and intra-operatively (i.e. before operation and during operation) by using an external coil 14, without the glasses 5, placed in close proximity to the retinal stimulation system 1. The coil 14 may communicate the status of the retinal stimulation system 1 to the VPU 20 that is connected to the Fitting System laptop 10 as shown in FIG. 10.

As discussed above, the VPU 20 processes the image from the camera 12 and transforms the image into electrical stimulation patterns for the retinal stimulation system. Filters such as edge detection filters may be applied to the electrical stimulation patterns for example by the VPU 20 to generate, for example, a stimulation pattern based on filtered video data that the VPU 20 turns into stimulation data for the retinal stimulation system. The images may then be reduced in resolution using a downscaling filter. In one exemplary embodiment, the resolution of the image may be reduced to match the number of electrodes in the electrode array 2010 of the retinal stimulation system. That is, if the electrode array has, for example, sixty electrodes, the image may be reduced to a sixty channel resolution. After the reduction in resolution, the image is mapped to stimulation intensity using for example a look-up table that has been derived from testing of individual subjects. Then, the VPU 20 transmits the stimulation parameters via forward telemetry to the retinal stimulation system in frames that may employ a cyclic redundancy check (CRC) error detection scheme.

In one exemplary embodiment, the VPU 20 is in constant communication with the retinal stimulation system through forward and backward telemetry. In this document, the forward telemetry refers to transmission from VPU 20 to the retinal stimulation system 1 and the backward telemetry refers to transmissions from the Retinal stimulation system 1 to the VPU 20. During the initial setup, the VPU 20 may transmit null frames (containing no stimulation information) until the VPU 20 synchronizes with the Retinal stimulation system 1 via the back telemetry. In one embodiment, an audio alarm may be used to indicate whenever the synchronization has been lost.

In order to supply power and data to the Retinal stimulation system 1, the VPU 20 may drive the external coil 14, for example, with a 3 MHz signal. To protect the subject, the retinal stimulation system 1 may comprise a failure detection circuit to detect direct current leakage and to notify the VPU 20 through back telemetry so that the visual prosthesis apparatus can be shut down.

The forward telemetry data (transmitted for example at 122.76 kHz) may be modulated onto the exemplary 3 MHz carrier using Amplitude Shift Keying (ASK), while the back telemetry data (transmitted for example at 3.8 kHz) may be modulated using Frequency Shift Keying (FSK) with, for example, 442 kHz and 457 kHz. The theoretical bit error rates can be calculated for both the ASK and FSK scheme assuming a ratio of signal to noise (SNR). The system disclosed in the present disclosure can be reasonably expected to see bit error rates of 10-5 on forward telemetry and 10-3 on back telemetry. These errors may be caught more than 99.998% of the time by both an ASIC hardware telemetry error detection algorithm and the VPU 20's firmware. For the forward telemetry, this is due to the fact that a 16-bit cyclic redundancy check (CRC) is calculated for every 1024 bits sent to the ASIC within electronics package 2014 of the Retinal Stimulation System 1. The ASIC of the Retinal Stimulation System 1 verifies this CRC and handles corrupt data by entering a non-stimulating 'safe' state and reporting that a telemetry error was detected to the VPU 20 via back telemetry. During the 'safe' mode, the VPU 20 may attempt to return the implant to an operating state. This recovery may be on the order of milliseconds. The back telemetry words are checked for a 16-bit header and a single parity bit. For further protection against corrupt data being misread, the back telemetry is only checked for header and parity if it is recognized as properly encoded Bi-phase Mark Encoded (BPM) data. If the VPU 20 detects invalid back telemetry data, the VPU 20 immediately changes mode to a 'safe' mode where the Retinal Stimulation System 1 is reset and the VPU 20 only sends non-stimulating data frames. Back telemetry errors cannot cause the VPU 20 to do anything that would be unsafe.

Figures 1, 12:
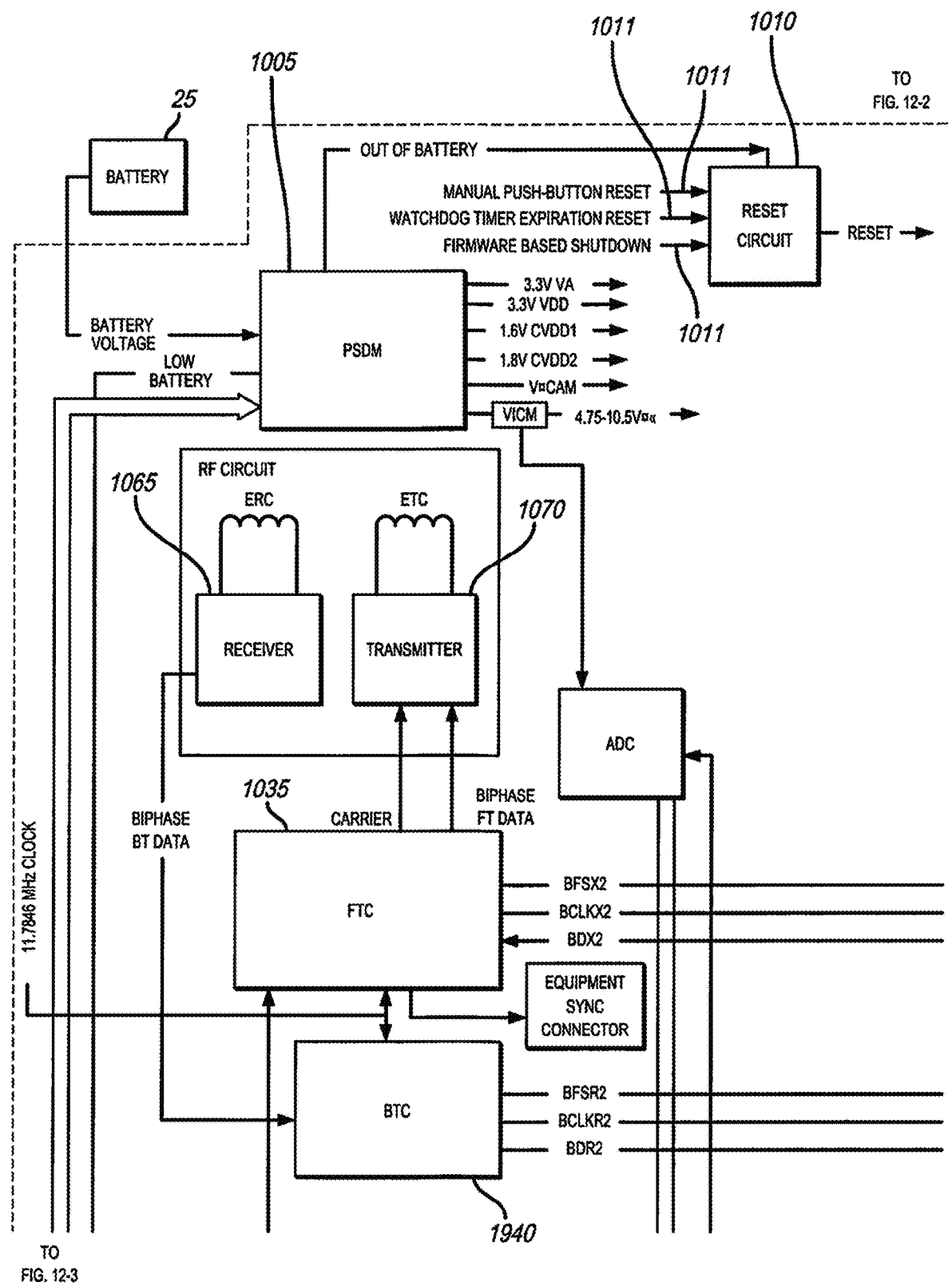
Figures 2, 12:
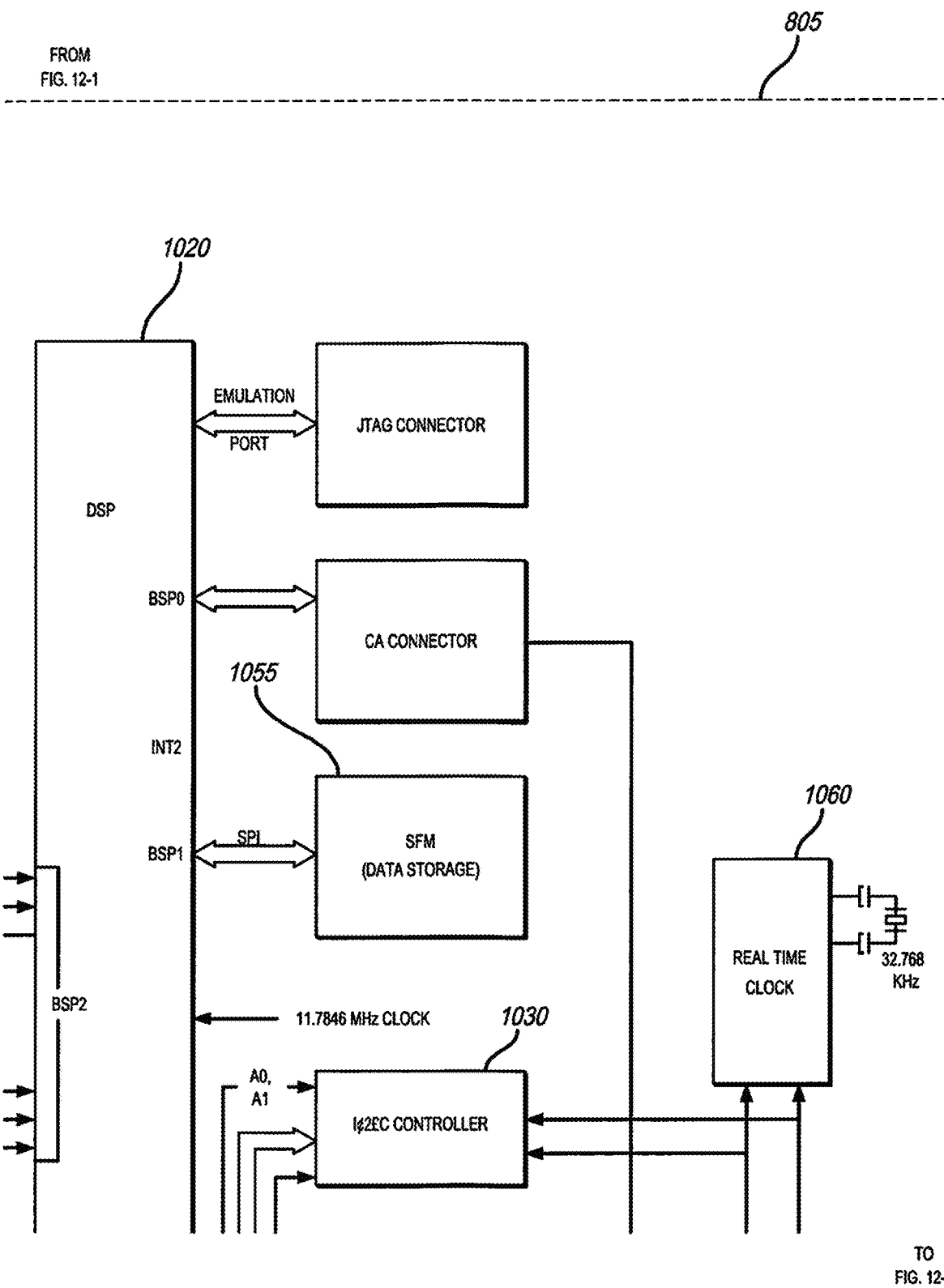
Figures 3, 12:
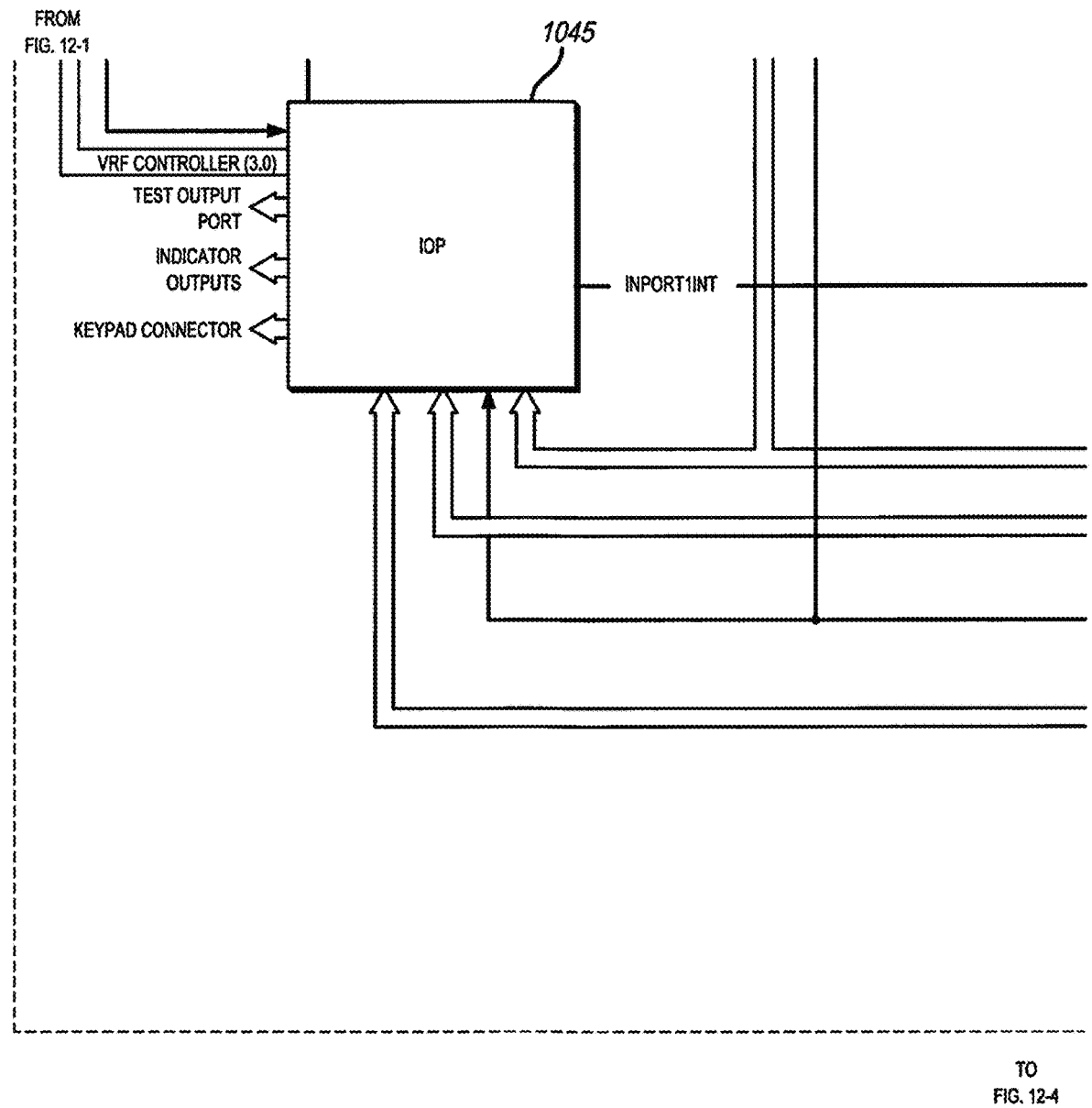
Figures 4, 12:
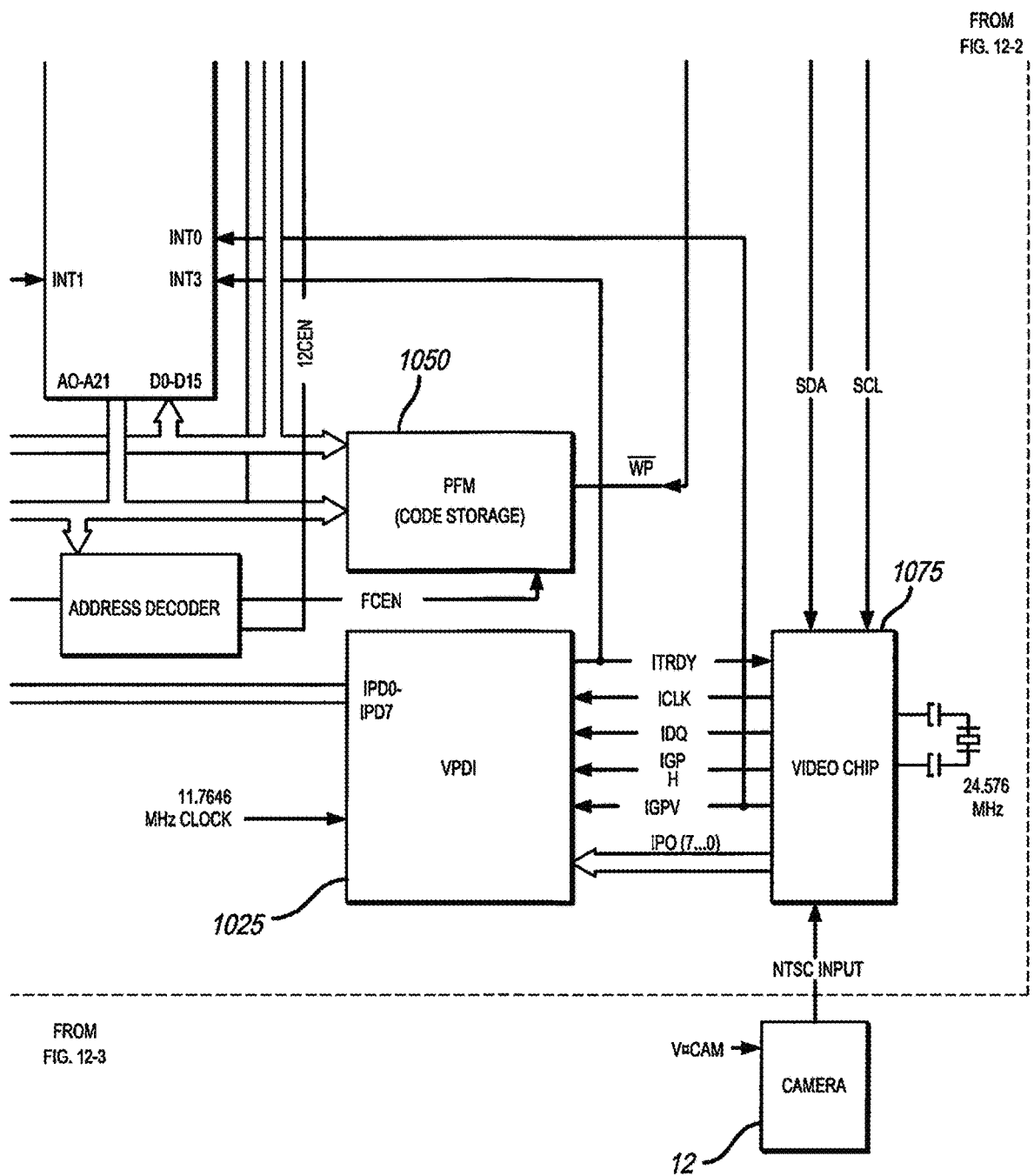

One exemplary embodiment of the VPU 20 is shown in FIG. 12. The VPU 20 may comprise: a Power Supply, a Distribution and Monitoring Circuit (PSDM) 1005, a Reset Circuit 1010, a System Main Clock (SMC) source (not shown), a Video Preprocessor Clock (VPC) source (not shown), a Digital Signal Processor (DSP) 1020, Video Preprocessor Data Interface 1025, a Video Preprocessor 1075, an I²C Protocol Controller 1030, a Complex Programmable Logic device (CPLD) (not shown), a Forward Telemetry Controller (FTC) 1035, a Back Telemetry Controller (BTC) 1040, Input/Output Ports 1045, Memory Devices like a Parallel Flash Memory (PFM) 1050 and a Serial Flash Memory (SFM) 1055, a Real Time Clock 1060, an RF Voltage and Current Monitoring Circuit (VIMC) (not shown), a speaker and/or a buzzer, an RF receiver 1065, and an RF transmitter 1070.

The Power Supply, Distribution and Monitoring Circuit (PSDM) 1005 may regulate a variable battery voltage to several stable voltages that apply to components of the VPU 20. The Power Supply, Distribution and Monitoring Circuit (PSDM) 1005 may also provide low battery monitoring and depleted battery system cutoff. The Reset Circuit 1010 may have reset inputs 1011 that are able to invoke system level rest. For example, the reset inputs 1011 may be from a manual push-button reset, a watchdog timer expiration, and/or firmware based shutdown. The System Main Clock (SMC) source is a clock source for DSP 1020 and CPLD. The Video Preprocessor Clock (VPC) source is a clock source for the Video Processor. The DSP 1020 may act as the central processing unit of the VPU 20. The DSP 1020 may communicate with the rest of the components of the VPU 20 through parallel and serial interfaces. The Video Processor 1075 may convert the NTSC signal from the camera 12 into a down-scaled resolution digital image format. The Video Processor 1075 may comprise a video decoder (not shown) for converting the NTSC signal into high-resolution digitized image and a video scaler (not shown) for scaling down the high-resolution digitized image from the video decoder to an intermediate digitized image resolution. The video decoder may be composed of an Analog Input Processing, Chrominance and Luminance Processing and Brightness Contrast and Saturation (BSC) Control circuits. The video scaler may be composed of Acquisition control, Pre-scaler, BSC-control, Line Buffer and Output Interface. The I²C Protocol Controller 1030 may serve as a link between the DSP 1020 and the I²C bus. The I²C Protocol Controller 1030 may be able to convert the parallel bus interface of the DSP 1020 to the I²C protocol bus or vise versa. The I²C Protocol Controller 1030 may also be connected to the Video Processor 1075 and the Real Time Clock 1060. The VPDI 1025 may contain a tri-state machine to shift video data from Video Preprocessor 1075 to the DSP 1020. The Forward Telemetry Controller (FTC) 1035 packs 1024 bits of forward telemetry data into a forward telemetry frame. The FTC 1035 retrieves the forward telemetry data from the DSP 1020 and converts the data from logic level to biphase marked data. The Back Telemetry Controller (BTC) 1040 retrieves the biphase marked data from the RF receiver 1065, decodes it, and generates the BFSR and BCLKR for the DSP 1020. The Input/Output Ports 1045 provide expanded JO functions to access the CPLD on-chip and off-chip devices. The Parallel Flash Memory (PFM) 1050 may be used to store executable code and the Serial Flash Memory (SFM) 1055 may provide Serial Port Interface (SPI) for data storage. The VIMC may be used to sample and monitor RF transmitter 1070 current and voltage in order to monitor the integrity status of the retinal stimulation system 1.

FIG. 13 shows a perspective view of the implanted portion of the preferred visual prosthesis. A flexible circuit 2001 includes a flexible circuit electrode array 2010 which is mounted by a retinal tack (not shown) or similar means to the epiretinal surface. The flexible circuit electrode array 2010 is electrically coupled by a flexible circuit cable 2012, which pierces the sclera and is electrically coupled to an electronics package 2014, external to the sclera.

The electronics package 2014 is electrically coupled to a secondary inductive coil 2016. Preferably the secondary inductive coil 2016 is made from wound wire. Alternatively, the secondary inductive coil 2016 may be made from a flexible circuit polymer sandwich with wire traces deposited between layers of flexible circuit polymer. The secondary inductive coil receives power and data from a primary inductive coil 14, which is external to the body. The electronics package 2014 and secondary inductive coil 2016 are held together by the molded body 2018. The molded body 18 holds the electronics package 2014 and secondary inductive coil 16 end to end. The secondary inductive coil 16 is placed around the electronics package 2014 in the molded body 2018. The molded body 2018 holds the secondary inductive coil 2016 and electronics package 2014 in the end to end orientation and minimizes the thickness or height above the sclera of the entire device. The molded body 2018 may also include suture tabs 2020. The molded body 2018 narrows to form a strap 2022 which surrounds the sclera and holds the molded body 2018, secondary inductive coil 2016, and electronics package 2014 in place. The molded body 2018, suture tabs 2020 and strap 2022 are preferably an integrated unit made of silicone elastomer. Silicone elastomer can be formed in a pre-curved shape to match the curvature of a typical sclera. However, silicone remains flexible enough to accommodate implantation and to adapt to variations in the curvature of an individual sclera. The secondary inductive coil 2016 and molded body 2018 are preferably oval shaped. A strap 2022 can better support an oval shaped coil. It should be noted that the entire implant is attached to and supported by the sclera. An eye moves constantly. The eye moves to scan a scene and also has a jitter motion to improve acuity. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 14:
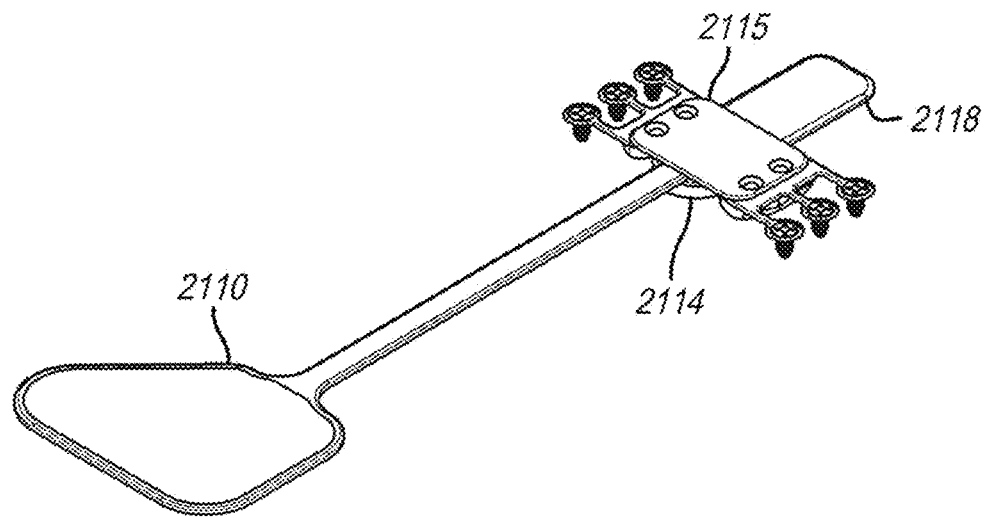
FIG. 14 is a perspective view of the implanted portion of a cortical visual prosthesis.
Figure 15:
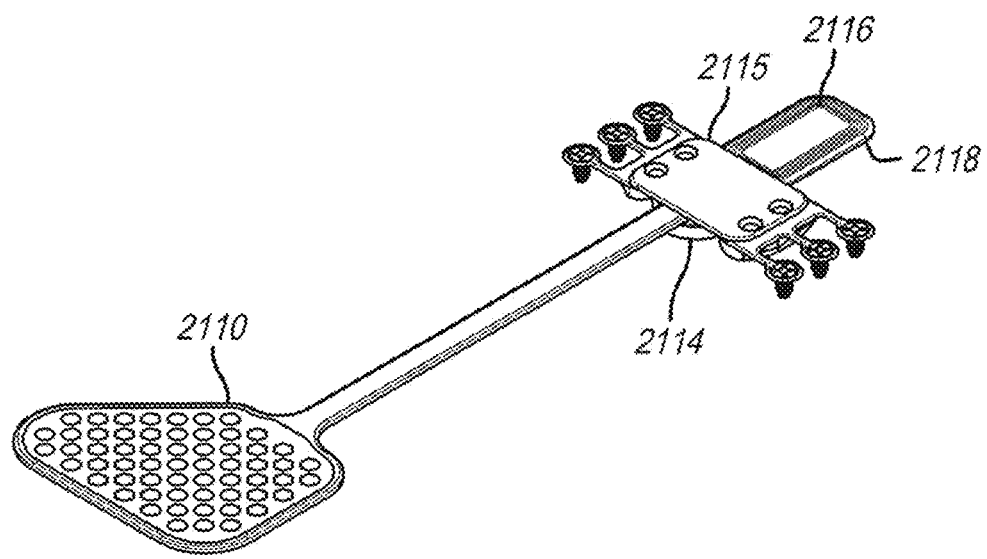
FIG. 15 is the perspective view of FIG. 20 adding the location of the electrodes and the coil.

While the description of the external portion of a visual prosthesis is described in terms of a retinal stimulator, the description is equally applicable to a cortical stimulator as shown in FIG. 14. FIG. 14 shows a perspective view of an implantable portion of a cortical visual prosthesis. FIG. 15 adds the locations of the electrodes and coil of the implantable portion. Note from this view the electrodes are show through the flexible circuit electrode array 2110. That is the electrodes are on the other side. It is advantageous that the flexible circuit electrode array 2110 be made in a trapezoidal shape with the cable portion attached to the smallest side of the trapezoid. This shape better accommodates the target tissue on the medial surface of the visual cortex. The molded body 2119 holding the electronics package 2114 and the coil 2116 is arranged with the coil 2116 opposite the flexible circuit electrode array 2110. The device is intended to be implanted with the flexible circuit electrode array 2110 attached on top of the package (toward the outside of the skull). This allows the electrodes to be on the same side of the flexible circuit electrode array 2110 as the bond pads connecting the flexible circuit electrode array 2110 to the electronics package 2114 and still face down toward the brain. The ceramic substrate portion of the electronics package 2114 to which the flexible circuit electrode array 2110 is attached is more delicate than the metal can portion. A mounting fixture 2115 covers and protects the electronics package 2114, provides screw tabs for attaching the electronics package 2114 to the skull and further provides a heat sink to dissipate heat from the electronics package 2114. The electronics package 2114, coil 2116 and molded body 2118 are implanted within a hollowed out portion of the skull. Preferably the hollowed out portion does not go entirely through the skull. Only a small slot is needed to feed the flexible circuit electrode array 1210 through to its implanted location. This provides better protection to the brain than an implant where large portions of the skull are removed. The overall device is preferably about 9.7 cm in length. The electrode array portion 110 is preferably about 2.4 cm by 3.4 cm. The coil and electronics molded body is preferably 1.1 cm or less in width. Each electrode is preferably about 2 mm in diameter.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

Accordingly, what has been shown is an improved visual prosthesis and an improved method for spatial fitting and image stabilization in a visual prosthesis. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A method of fitting a visual prosthesis comprising:

Providing a visual prosthesis including a neural stimulator adapted to be implanted in a user's body including electrodes, a visual processor, adapted to be external to the user's body, glasses adapted to be external to the user's body and supported by the user's nose and ears, and an pupil location sensor adapted to be external to the user's body and supported by the glasses measuring pupil gaze;

stimulating percepts in a subject by applying an electrical current from the neural stimulator to neural tissue with a test group of the electrodes at an actual location;

asking the subject to look in the direction the subject perceives the percept resulting from applying the electrical current to the neural tissue;

recording a starting pupil location, prior to stimulation, and a pupil location after stimulation to calculate a perceived location;

recording the perceived location with the pupil location sensor;

calculating a difference between the actual location and the perceived location in a computer; and adjusting a spatial map in the video processor of the visual prosthesis based on the difference.

2. The method according to claim 1, wherein the step of recording a perceived location is recording a location after stimulation relative to a starting location before stimulation.

3. The method according to claim 1, wherein the step of recording a perceived location is recording an absolute location after stimulation.

4. The method according to claim 1, wherein the pupil location sensor is a camera.

5. The method according to claim 4, wherein the pupil location sensor is an IR camera and the visual prosthesis further comprises an IR illuminator illuminating the user's eye.

6. The method according to claim 1, wherein the pupil location sensor blocks a user's natural field of view.

* * * * *